United States Patent [19]
Wätjen et al.

[11] Patent Number: 4,772,696
[45] Date of Patent: Sep. 20, 1988

[54] OXADIAZOLYL IMIDAZOBENZODIAZEPINE PROCESS

[75] Inventors: Frank Wätjen, Bagsvaerd; Mogens Engelstoft, Vaerlose; John B. Hansen, Lyngby; Leif H. Jensen, Hellerup, all of Denmark

[73] Assignee: A/S Ferrosan, Soborg, Denmark

[21] Appl. No.: 942,162

[22] Filed: Dec. 16, 1986

Related U.S. Application Data

[62] Division of Ser. No. 837,100, Mar. 6, 1986, Pat. No. 4,670,433.

[30] Foreign Application Priority Data

| Mar. 8, 1985 | [DK] | Denmark | 1080/85 |
| Mar. 8, 1985 | [DK] | Denmark | 1081/85 |
| May 17, 1985 | [DK] | Denmark | 2203/85 |
| May 17, 1985 | [DK] | Denmark | 2204/85 |
| Oct. 17, 1985 | [DK] | Denmark | 4769/85 |

[51] Int. Cl.$^4$ .................................. C07D 521/00
[52] U.S. Cl. ............................. 540/498; 540/504; 540/506
[58] Field of Search ................................ 540/498

[56] References Cited

FOREIGN PATENT DOCUMENTS 150040 7/1985 European Pat. Off. ............ 540/498

*Primary Examiner*—Robert T. Bond
*Attorney, Agent, or Firm*—Gordon W. Hueschen

[57] ABSTRACT

New oxadiazolyl imidazobenzodiazepine derivatives having the formula

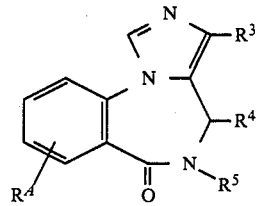

wherein $R^3$ has the formula

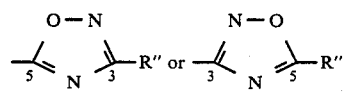

wherein
R" is hydrogen, $C_{1-6}$ alkyl $C_{1-6}$ alkoxymethyl or $C_{3-6}$-cycloalkyl;
$R^4$ is hydrogen;
$R^5$ is $C_{1-6}$ alkyl or $R^4$ and $R^5$ together form a 2–4 membered alkylene bridge; and $R^A$ is $C_{1-6}$ alkyl, $C_{1-6}$ alkoxy, or $C_{1-3}$ trifluoroalkyl, pharmaceutical compositions thereof, and method of treating therewith, are disclosed.

The compounds and pharmaceutical compositions are useful in the amelioration, mitigation, or elimination of central nervous system disorders related to benzodiazepine receptors and especially as anticonvulsants, anxiolytics, hypnotics, and nootropics.

1 Claim, No Drawings

OXADIAZOLYL IMIDAZOBENZODIAZEPINE PROCESS

This is a division of application Ser. No. 837,100 filed Mar. 6, 1986.

FIELD OF INVENTION

This invention relates to new oxadiazolyl imidazobenzodiazepine derivatives, to a method of preparing them, to pharmaceutical compositions thereof, and to a method of treating therewith. These new compounds and pharmaceutical compositions thereof are useful for the amelioration, mitigation, alleviation, or elimination of central nervous system disorders or ailments related to benzodiazepine receptors, and especially in psychopharmaceutical preparations as anticonvulsants, anxiolytics, and nootropics due to their high capacity for binding to benzodiazepine receptors.

BACKGROUND OF INVENTION AND PRIOR ART

The most relevant prior art is to be found in European Patent Application No. 109,921 in which other oxadiazolyl derivatives of imidazobenzodiazepines are disclosed. The compounds are described as being able to displace flunitrazepam from benzodiazepine receptors.

European Patent Application No. 150,040 also discloses oxadiazolyl derivatives of imidazobenzodiazepines. Although the generic claims of that patent application include compounds having the general formula II

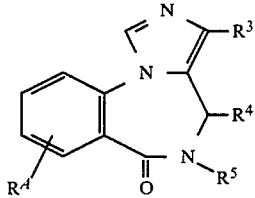

wherein $R^3$, $R^4$, $R^5$, and $R^A$ have meanings as defined below, this European Patent Application No. 150,040 does not disclose any examples of compounds wherein $R^A$ is alkoxy or lower alkyl.

OBJECTS OF THE INVENTION

It is an object of the present invention to provide certain novel oxadiazole imidazobenzodiazepines and pharmaceutically-acceptable acid addition salts thereof, which are useful in the treatment of central nervous system disorders or ailments, especially as anticonvulsants, anxiolytics, and nootropics, a process for producing the same, pharmaceutical compositions thereof, intermediates therefor, and a method of treating therewith. Additional objects will become apparent hereinafter, and still others will be obvious to one skilled in the art.

SUMMARY OF THE INVENTION

The invention, then, comprises the following, inter alia: certain novel oxadiazole imidazobenzodiazepines as set forth in the following formula, pharmaceutical compositions thereof, a method of treating a central nervous system ailment in a subject in need of such treatment comprising the step of administering to the said subject an amount of such a compound which is effective for the alleviation of such ailment, preferably wherein the compound is administered in the form of a pharmaceutical composition thereof in which it is present together with a pharmaceutically-acceptable carrier or diluent, as well as an intermediate compound having the formula $CN—CH_2—R^3$ wherein $R^3$ has the meaning defined below in formula I, and a method of preparing such pharmacologically-active compounds.

THE PRESENT INVENTION

It has been found that the novel compounds of the present invention have improved pharmaceutical properties when compared to well-known related compounds.

The new compounds of the present invention are oxadiazolyl imidazobenzodiazepine derivatives having the general formula I:

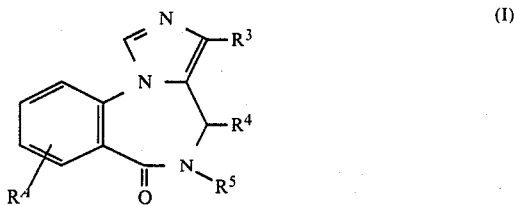

wherein $R^3$ has the formula

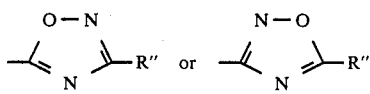

wherein

R" is hydrogen, $C_{1-6}$ alkyl, $C_{1-6}$ alkoxymethyl, or $C_{3-6}$ cycloalkyl;

$R^4$ is hydrogen;

$R^5$ is $C_{1-6}$ alkyl or $R^4$ and $R^5$ together form a 2–4 membered alkylene bridge; and $R^A$ is $C_{1-6}$ alkyl, $C_{1-6}$ alkoxy, or $C_{1-3}$ trifluoroalkyl.

It is well known (Squires, R. F. and Braestrup, C., Nature (London) 266, 734 (1977)) that specific sites in the central nervous systems of vertebrates exhibit a high specific affinity for binding 1,4 and 1,5-benzodiazepines. These sites are called benzodiazepine receptors.

The pharmaceutical potency of the compounds of the present invention is evidenced by determining their capability for displacing radioactively-labelled flunitrazepam and the imidazobenzodiazepine $^3$H-Ro 15-1788 from such benzodiazepine receptors.

The displacement activity of the compounds of the invention has been determined by determining their $IC_{50}$ and $ED_{50}$ values. The $IC_{50}$ value represents the concentration (nM, 30° C.) which causes a displacement of 50% of the specific binding of $^3$H-Ro 15-1788 in samples comprising a total volume of 1 ml.

The displacement test is performed as follows:

750 μl of rat cerebral cortical membrane homogenate was incubated with 100 μl of 5 nM $^3$H-Ro 15-1788 in water at 30° C. Then 100 μl of a solution of the test compound and 50 μl of Krebs buffer was added. After incubation the binding reaction was terminated by filtration through Whatman GF/B glass fibre filters followed by 2×5 ml wash with ice-cold buffer and the radioactivity was measured by scintillation counting.

The IC$_{50}$ was determined by including at least four concentrations of the test compound and log/probit analysis of the resulting data.

The ED$_{50}$ value represents the dose (mg/kg) of a test substance which causes the specific binding fo flunitrazepam to benzodiazepine receptors in a living brain to be reduced to 50% of the control value.

Such an in vivo test is carried out as follows:

Groups of mice are injected with the test substance at different doses and usually subcutaneously. Fifteen minutes later $^3$H-flunitrazepam is given intravenously to the mice and, after a further twenty minutes, the mice are killed. Their forebrain membranes are removed and the radioactivity of these forebrain membranes is measured by scintillation counting. The ED$_{50}$ value is determined from dose-response curves.

The results obtained in the above-described tests for some of the compounds of the invention will appear from the following Table 1.

The invention also relates to a method of preparing the above-identified compounds. This method comprises the steps of:

(a) reacting a reactive derivative of a compound having the general formula III

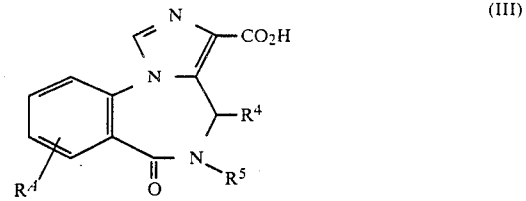

wherein R$^4$, R$^5$, and R$^A$ have the meanings set forth above, with a compound having the formula

TABLE 1

(I)

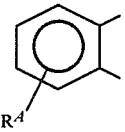

| R$^A$ | R$^4$ | R$^5$ | R$^3$ | in vitro IC$_{50}$ nm | in vivo ED$_{50}$ mg/kg |
|---|---|---|---|---|---|
| 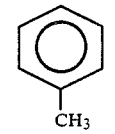 | H | CH$_3$ | 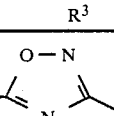 | 44.8 | 2.2 |
| 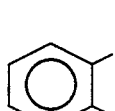 | —CH$_2$CH$_2$— | | 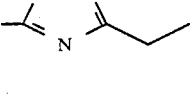 | 30 | 0.4 |
| 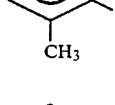 | —CH$_2$CH$_2$— | | 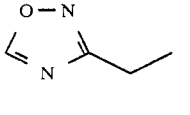 | 23 | 0.2 |
| 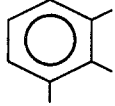 | H | CH$_3$ | 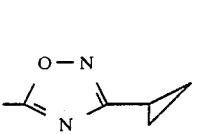 | 5.6 | 0.5 |
| 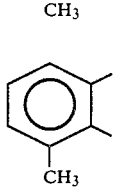 | H | CH$_3$ | 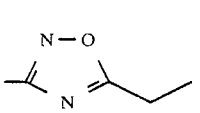 | — | 4.0 |

Method in General

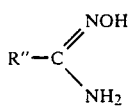
(IV)

wherein R" has the meaning set forth above to form a compound having the formula I in which R³ is

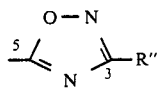

wherein R" has the meaning set forth above, or (b) reacting a compound having the general formula V

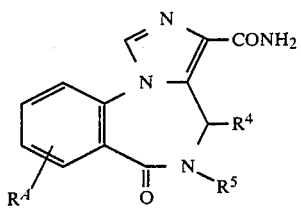
(V)

wherein R^A, R⁴ and R⁵ have the meanings set forth above, with a compound of the formula VI

R"—C(OCH₃)₂N(CH₃)₂ (VI)

wherein R" has the meaning set forth above, to form a compound having the general formula VII

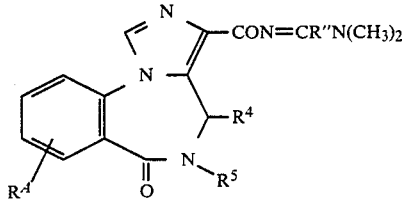
(VII)

wherein R^A, R⁴, R⁵ and R" have the meanings set forth above, and reacting the compound having the formula VII with NH₂OH or another aminating agent to form a compound having the formula I in which R³ is

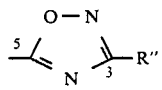

wherein R" has the meaning set forth above, or (c) reacting a compound having the general formula VIII

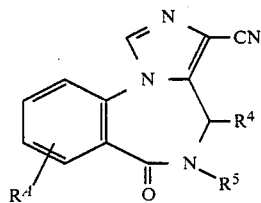
(VIII)

wherein R^A, R⁴, and R⁵ have the meanings set forth above, with NH₂OH to form a compound having the general formula IX

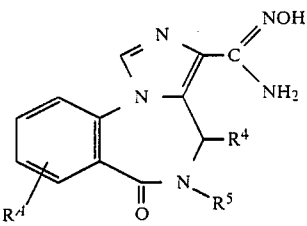
(IX)

wherein R^A, R⁴, and R⁵ have the meanings set forth above, and reacting the compound having the formula IX with a compound having the general formula X (R"CO)₂O (X)

wherein R" has the meaning set forth above, to form a compound having the formula I in which R³ is

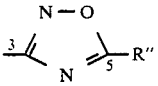

wherein R" has the meaning set forth above, or (d) reacting a compound having the general formula XI

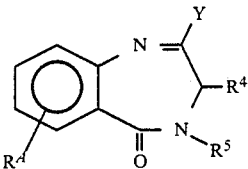
(XI)

wherein R⁴, R⁵, and R^A have the meanings defined above, and Y is a leaving group, with a compound having the formula XII

CN—CH₂—R³ (XII)

wherein R³ has the meaning defined above, to form a compound having the formula I.

The substituent Y may be any suitable leaving group, such as the —OP(O)(O-ethyl)₂ group of Example 5(c) hereof. Alternatively, the leaving group may be any disclosed in U.S. Pat. Nos. 4,031,079 or 4,359,420, for example, halogen, alkylthio, e.g., methylthio, aralkylthio, N-nitrosoalkylamino, alkoxy, mercapto, —OP(O)(OR)₂ wherein R is lower-alkyl or —OP(O)(NR'R") wherein R' and R" each represents lower-alkyl, allyl, or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty (−40) degrees Celsius to about room temperature is accordingly usually particularly suitable.

The starting materials for the foregoing reactions are known or readily preparable from commercially available benzene derivatives using the methods described in European Patent Applications Nos. 109,921 and 27,214 and in Synthesis, Vol. 10, pp. 681–682.

DETAILED DESCRIPTION OF THE INVENTION

The preparation of the compounds of the invention will now be described in further detail with reference to the following Examples, which are given by way of illustration only and are not to be construed as limiting.

EXAMPLE I

A. Isatoic anhydride 7.5 g of 2-aminobenzoic acid hydrochloride was mixed with 10 ml of diphosgene and the mixture was stirred in 150 ml dioxane for 40 minutes at reflux. The resulting mixture was cooled and filtered.

Yield: 5.7 g of title compound.

In the same manner, from the appropriate amino benzoic acids, the following compounds are synthesized:
6-methylisatoic anhydride,
6-methoxyisatoic anhydride, and
6-trifluoromethylisatoic anhydride,
5-methylisatoic anhydride,
5-methoxyisatoic anhydride, and
5-trifluoromethylisatoic anhydride.

B. 3,4-dihydro-4-methyl-2H-1,4-benzodiazepine-2,5(1H)-dione 64.8 g of isatoic acid anhydride was mixed with 35.4 g of sarcosine and the resulting mixture stirred with 420 ml dimethylsulfoxide at 100° C. for 4 hours. The mixture was cooled and was poured into 1.5 l water. The precipitated product was washed with water and dried. Yield: 57.1 g of title compound.

In the same manner, from appropriate isatoic anhydride derivatives, the following compounds are synthesized.
6-methoxy-3,4-dihydro-4-methyl-2H-1,4-benzodiazepine-2,5(1H)-dione
(S)-6-methyl-1,2,3,11a-tetrahydro-5H-pyrrolo(2,1-c)(1,4)benzodiazepine-5,11(10H)-dione by reaction with L-proline. M.p. 207.6°–209.9° C.
6-trifluoromethyl-3,4-dihydro-4-methyl-2H-1,4-benzodiazepine-2,5(1H)dione. M.p. 223.7°–225.9° C.
7-methyl-3,4-dihydro-4-methyl-2H-1,4-benzodiazepine-2,5(1H)-dione. M.p. 260.0°–260.6° C.
(S)-7-methyl-1,2,3,11a-tetrahydro-5H-pyrrolo(2,1-c)(1,4)benzodiazepine-5,11(10H)-dione by reaction with L-proline. M.p. 243.1–244.5° C.
6-methyl-3,4-dihydro-4-methyl-2H-1,4-benzodiazepine-2,5(1H)-dione. M.p. 204.4°–205.4° C.
(S)-6-methyl-1,10a-dihydro-azeto(2,1-c)(1,4)benzodiazepine-4,10-(2H,9H)-dione by reaction with L-azetidine
7-methoxy-3,4-dihydro-4-methyl-2H-1,4-benzodiazepine-2,5(1H)-dione. M.p. 206° C.
(S)-7-methoxy-1,2,3,11a-tetrahydro-5H-pyrrolo(2,1-c)(1,4)benzodiazepine-5,11(10H)-dione by reaction with L-proline. M.p. 216.8°–217.6° C.
(S)-5-methyl-1,10a-dihydro-azeto(2,1-c)(1,4)benzodiazepine-4,10-(2H,9H)-dione by reaction with L-azetidine
7-trifluoromethyl-3,4-dihydro-4-methyl-2H-1,4-benzodiazepine-2,5(1H)-dione
9-methyl-3,4-dihydro-4-methyl-2H-1,4-benzodiazepine-2,5(1H)-dione C. Ethyl 5,6-dihydro-5-methyl-6-oxo-4H-imidazo(1,5-a)(1,4)-benzodiazepine-3-carboxylate 16.5 g of 4-methyl-3,4-dihydro-2H-1,4-benzodiazepine-2,5(1H)-dione and 11.7 g of K-t-butoxide was dissolved in 100 ml of dry dimethyl formamide (DMF) and the mixture was stirred for 10 minutes. Then 13.2 ml of diethylchlorophosphate was added and the resulting mixture was cooled to −20° C. and stirred for 10 minutes.

A mixture of 10.8 g K-t-butoxide and 10.5 ml ethyl isocyanoacetate in 30 ml of dry DMF was added to the above prepared mixture at −10° to −20° C. and the resulting mixture was stirred for one hour at RT, whereafter it was poured into 8.7 ml acetic acid in 300 ml water. This mixture was extracted 2 times with 150 ml methylene chloride. The organic phase was dried and evaporated. The resulting residue was crystallized leaving 10 g of the title compound as crystals.

In the same manner, from the appropriate benzodiazepine-diones, the following compounds are synthesized.
Ethyl 5,6-dihydro-5-methyl-6-oxo-7-methoxy-4H-imidazo(1,5-a)(1,4)benzodiazepine-3-carboxylate.
Ethyl (S)-8-methyl-11,12,13,13a-tetrahydro-9-oxo-9H-imidazo(1,5-a)pyrrolo(2,1-c)(1,4)benzodiazepine-1-carboxylate. M.p. 150.4°–150.5° C.
Ethyl 5,6-dihydro-5-methyl-6-oxo-7-methoxy-4H-imidazo(1,5-a)(1,4)benzodiazepine-3-carboxylate as an oil
Ethyl 8-methyl-5,6-dihydro-5-methyl-6-oxo-4H-imidazo(1,5-a)(1,4)benzodiazepine-3-carboxylate. M.p. 195.5°–195.8° C.
Ethyl (S)-7-methyl-11,12,13,13a-tetrahydro-9-oxo-9H-imidazo(1,5-a)pyrrolo(2,1-c)(1,4)benzodiazepine-1-carboxylate. M.p. 271.0°–271.7° C.
Ethyl 7-methyl-5,6-dihydro-5-methyl-6-oxo-4H-imidazo(1,5-a)(1,4)benzodiazepine-3-carboxylate. M.p. 147.7°–148.1° C.
Ethyl (S)-7-methyl-10,11,12,12a-tetrahydro-9-oxo-9H-imidazo(1,5-a)azeto(2,1-c)(1,4)benzodiazepine-1-carboxylate. M.p. 257.6°–259.1° C.
Ethyl 8-methoxy-5,6-dihydro-5-methyl-6-oxo-4H-midazo(1,5-a)(1,4)benzodiazepine-3-carboxylate. M.p. 228.1° C.
Ethyl (S)-7-methoxy-11,12,13,13a-tetrahydro-9-oxo-9H-imido(1,5-a)pyrrolo(2,1-c)(1,4)benzodiazepine-1-carboxylate. M.p. 196.6°–197.1° C.
Ethyl (S)-8-methyl-10,11,12,12a-tetrahydro-9-oxo-9H-imidazo(1,5-a)azeto(2,1-c)(1,4-benzodiazepin-1-carboxylate. M.p. 166.0° C.
Ethyl 7-methoxy-5,6-dihydro-5-methyl-6-oxo-4H-imidazo(1,5-a)(1,4)benzodiazepine-3-carboxylate as an oil.
Ethyl 10-methyl-5,6-dihydro-5-methyl-6-oxo-4H-imidazo(1,5-a)(1,4)benzodiazepine-3-carboxylate. M.p. 196.3°–196.9° C.

D. Methoxyacetamide oxime 2.3 g of sodium in 33 ml of dry methanol and 6.65 g of hydroxylamine hydrochloride in 66 ml of dry methanol was mixed. To the filtrate was added dropwise 7.8 g methoxyacetonitrile. The mixture was left for 48 hours.

The mixture was then cooled to 4° C. Filtration and evaporation of the filtrate gave 8.7 g of the title compound.

In the same manner, from appropriate nitriles, the following compounds are synthesized.
propionamide oxime
isopropyl carboxamide oxime
acetamide oxime
valerylamide oxime
cyclopropyl carboxamide oxime E. 3-(5-(3-methoxymethyl-1,2,4-oxadiazol)-yl)-5,6-dihydro-5-methyl-6-oxo-4h-imidazo[1,5-a][1,4]benzo-benzodiazepine 240 mg of sodium was dissolved in 12 ml of dry ethanol with 4 g of molecular sieves (4 Å). 2.2 g of methoxyacetamide oxime and 1 g of ethyl 5,6-dihydro-5-methyl-6-oxo-4H-imidazo(1,5-a)(1,4)-benzodiazepine-3-carboxylate in 5 ml of dry ethanol was added. This mixture was refluxed for 15 hours and was then evaporated. The residue was recrystallized from water yielding 0.6 g of the title compound.
M.p. 193.8°–194.1° C.

In the same manner the following compounds are synthesized from the appropriate carboxylate.

3-(5-(3-ethyl-1,2,4-oxadiazol)-yl)-8-trifluoromethyl-5,6-dihydro-5methyl-6-oxo-4H-imidazo(1,5-a)(1,4)benzodiazepine
M.p. 172°–175° C.

3-(5-(3-ethyl-1,2,4-oxadiazol)-yl)-8-methyl-5,6-dihydro-5-methyl-6-oxo-4H-imidazo(1,5-a)(1,4)benzodiazepine
M.p. 195.4°–195.7° C.

(S)-1-(5-(3-ethyl-1,2,4-oxadiazol)-yl)-7-methyl-11,12,13,13a-tetrahydro-9-oxo-9H-imidazo(1,5-a)pyrrolo(2,1-c)(1,4)-benzodiazepine M.p. 270° C.

3-(5-(3-methoxymethyl-1,2,4-oxadiazol)-yl)-8-methyl-5,6-dihydro-5-methyl-6-oxo-4H-imidazo(1,5-a)(1,4)benzodiazepine
M.p. 215.3°–216.1° C.

(S)-1-(5-(3-ethyl-1,2,4-oxadiazol)-yl)-8-methyl-11,12,13,13a-tetrahydro-9-oxo-9H-imidazo(1,5-a)pyrrolo(2,1-c)(1,4)-benzodiazepine
M.p. 170.3°–170.5° C.

3-(5-(3-ethyl-1,2,4-oxadiazol)-yl)-7-methyl-5,6-dihydro-5-methyl-6-oxo-4H-imidazo(1,5-a)(1,4)benzodiazepine
M.p. 164.1° C.

(S)-1-(5-(3-ethyl-1,2,4-oxadiazol)-yl)-7-methyl-10,11,12,12a-tetrahydro-9-oxo-9H-imidazo(1,5-a)azeto(2,1-c)(1,4)benzodiazepine
M.p. 210.1°–212.4° C.

(S)-1-(5-(3-isopropyl-1,2,4-oxadiazol)-yl)-7-methyl-10,11,12,12a-tetrahydro-9-oxo-9H-imidazo(1,5-a)azeto(2,1-c)(1,4)-benzodiazepine
M.p. 193.4°–195.4° C.

3-(5-(3-methyl-1,2,4-oxadiazol)-yl)-8-methoxy-5,6-dihydro-5-methyl-6-oxo-4H-imidazo(1,5-a)(1,4)benzodiazepine
M.p. 222°–222.3° C.

3-(5-(3-ethyl-1,2,4-oxadiazol)-yl)-8-methoxy-5,6-dihydro-5-methyl-6-oxo-4H-imidazo(1,5-a)(1,4)benzodiazepine
M.p. 209.3°–210.4° C.

(S)-1-(5-(3-ethyl-1,2,4-oxadiazol)-yl)-7-methoxy-11,12,13,13a-tetrahydro-9 -oxo-9H-imidazo(1,5-a)pyrrolo(2,1-c)(1,4)benzodiazepine
M.p. 237°–238° C.

(S)-1-(5-(3-ethyl-1,2,4-oxadiazol)-yl)-8-methyl-10,11,12,12a-tetrahydro-9-oxo-9H-imidazo(1,5-a)azeto(2,1-c)(1,4)benzodiazepine
M.p. 204.4°–204.6° C.

3-(5-(3-ethyl-1,2,4-oxadiazol)-yl)-7-methoxy-5,6-dihydro-5-methyl-6-oxo-4H-imidazo(1,5-a)(1,4)benzodiazepine
M.p. 211.3°–213.0° C.

3-(5-(3-ethyl-1,2,4-oxadiazol)-yl)-10-methyl-5,6-dihydro-5-methyl-6-oxo-4H-imidazo(1,5-a)(1,4)benzodiazepine. M.p. 162.6°–163.3° C.

(S)-1-(3-cyclopropyl-1,2,4-oxadiazol-5-yl)-8-methyl-11,12,13,13a-tetrahydro-9-oxo-9H-imidazo(1,5-a)pyrrolo(2,1-c)(1,4)benzodiazepine
M.p. 171.1°–171.2° C.

3-(3-cyclopropyl-1,2,4-oxadiazol-5-yl)-5,6-dihydro-5-methyl-6-oxo-7-methoxy-4H-imidazo(1,5-a)(1,4)benzodiazepine
M.p. 161.3° C.

3-(3-cyclopropyl-1,2,4-oxadiazol-5-yl)-5,6-dihydro-5-methyl-6-oxo-7-methyl-4H-imidazo(1,5-a)(1,4)benzodiazepine
M.p. 152.5°–153.1° C.

3-(3-isopropyl-1,2,4-oxadiazol-5-yl)-5,6-dihydro-5-methyl-6-oxo-7-methyl-4H-imidazo(1,5-a)(1,4)benzodiazepine
M.p. 173.2°–175.9° C.

(S)-1-(3-cyclopropyl-1,2,4-oxadiazol-5-yl)-8-methyl-10,11,12,12a-tetrahydro-9-oxo-9H-imidazo(1,5-a)azeto(2,1-c)(1,4)benzodiazepine
M.p. 173.1°–174.5° C.

EXAMPLE 2

A. 3-carbamoyl-8-methyl-5,6-dihydro-5-methyl-6-oxo-4H-imidazo-(1,5-a)(1,4)benzodiazepine A mixture of 3.5 g imidazole and 0.95 ml thionylchloride was stirred for 15 min in 35 ml of tetrahydrofurane. The mixture was filtered and the filtrate was added to 1.7 g of 8-methyl-5,6-dihydro-5-methyl-6-oxo-4H-imidazo(1,5-a)(1,4)benzodiazepine-3-carboxylic acid in 4 ml DMF. This mixture was stirred for 2 hours at RT and NH$_3$-gas was led to the mixture for 15 min. This mixture was then reduced to 15 ml and 100 ml of water was added. The precipitate was washed with water. Yield 1.6 g.
M.p. 290°–294° C.

B. 3-cyano-8- methyl-5,6-dihydro-5-methyl-6-oxo-4H-imidazo(1,5-a)(1,4)benzodiazepine 0.4 ml Br$_2$ in 10 ml methylene chloride was added to a solution of triphenyl phosphine in 40 ml methylene chloride at 0° C. To this mixture the product of A was added together with 3.3 ml triethylamine. This mixture was stirred at RT for 30 min. Then 100 ml of water was added. The organic phase was reduced to 20 ml at reduced pressure and 1.2 g of the title compound precipitated by adding 50 ml of ether.
M.p. 252°–252.3° C.

C. 8-methyl-5,6-dihydro-5-methyl-6-oxo-4H-imidazo(1,5-a)(1,4)benzodiazepine-3-carboxamide oxime.

1.2 g of the product of B, 600 mg of hydroxyl amine hydrochloride and 600 mg of potassium carbonate was stirred in 50 ml 96% ethanol and 2 ml of water at 50° C. for 4 hours. Then further 300 mg of hydroxyl amine hydrochloride was added and the mixture was stirred for 1 hour. The mixture was then reduced at reduced pressure to 20 ml and 50 ml water was added whereupon 1,2 g of the title compound precipitated M.p. 227°–229° C.

D. 3-(5-ethyl-1,2,4-oxadiazol-3-yl)-8-methyl-5,6-methyl-6-oxo-4H-imidazo(1,5-a)(1,4)benzodiazepine A mixture of 450 mg of the product of C and 15 ml propionic anhydride was stirred at 100° C. for 10 min. Then 25 ml of dry ethanol, 3 g molecular sieves (3 Å) and 50 mg of sodium was added and the resulting mixture was refluxed for 4 hours. The mixture was then filtered and the filtrate was reduced to 10 ml. Then 70 ml of water was added whereupon the title compound precipitated. The precipitate was washed with water and petroleum ether. Yield 150 mg. M.p. 174.6°–176.4° C.

In the same manner by reaction with acetic anhydride the following compounds are synthesized.

3-(3-(5-methyl-1,2,4-oxadiazol-3-yl)-8-methyl-5,6-dihydro-5-methyl-6-oxo-4H-imidazo(1,5-a)(1,4)benzodiazepine M.p. 276° C. dec.

EXAMPLE 3

3-(5-ethyl-1,2,4-oxadiazol-3-yl)-5,6-dihydro-5-methyl-6-oxo-4H-7-trifluoromethyl-imidazo(1,5-a)(1,4)benzodiazepine.

3,4-dihydro-4-methyl-6-trifluoromethyl-2H-1,4-benzodiazepine-2,5(1H)dione (2 mmol) was dissolved in 15 ml of dry dimethyl formamide (DMF) and charged with 2.5 mmol of K-t-butylate. This solution was cooled under $N_2$ to 20° C., whereafter 2.6 mmol of chlorodiethylphosphate was added.

The reaction mixture was kept under $N_2$ with stirring at $-20°$ C. and charged with a $-30°$ C. cold solution of 5-ethyl-3-isocyanomethyl-1,2,4-oxadiazole (2.7 mmol) and K-t-butylate 2.6 mmol in 15 ml dry DMF.

The resulting mixture was allowed to heat to room temperature, whereafter it was evaporated to dryness in vacuo. The oily residue was treated with $H_2O$/ether. The organic phase was evaporated to dryness in vacuo and the residue was crystallized from diethyl ether giving 50 mg of the title compound.

M.p. 230.4°–231.3° C.

EXAMPLE 3A 3-(3-ethyl-1,2,4-oxadiazol-5-yl)-7-methyl-5,6-dihydro-5-methyl-6-oxo-4-H-imidazo[1,5-a][1,4]benzodiazepine In exactly the same manner, by reaction with 3-ethyl-5-isocyanomethyl-1,2,4-oxadiazole, the compound 3-(3-ethyl-1,2,4-oxadizaol-5-yl)-7-methyl-5,6-dihydro-5-methyl-6-oxo-4-H-imidazo[1,5-a][1,4]benzodiazepine, M.p. 164° C., is produced from 6-methyl-3,4-dihydro-4-methyl-2H-1,4-benzodiazepine-2,5(1H)-dione.

EXAMPLE 4

3-cyclopropyl-5-isocyanomethyl-1,2,4-oxadiazole a 3-cyclopropyl-5-formylaminomethyl-1,2,4-oxadiazole.

A solution of ethyl formylaminomethyl-carboxylate (150 mmol) and cyclopropylcarboxamidoxime (100 mmol) in 100% EtOH (100 ml) was charged with Na (200 mg) and a crushed molecular sieve (4 Å) (10 g). The stirred reaction mixture was heated to reflux for 8 h. The mixture was cooled to room temperature, filtered through filter aid and the filtrate was evaporated in vacuo. The oily residue was partitioned into a $CHCl_3$ phase, dried with $Na_2SO_4$, and evaporated.

b 3-cyclopropyl-5-isocyanomethyl-1,2,4-oxadiazole

A stirred solution of 3-cyclopropyl-5-formylaminomethyl-1,2,4-oxadiazole (60 mmol) and triethylamine (176 mmol) in $CH_2Cl_2$ (100 ml) was charged at 0° C. dropwise with $POCl_3$ (60 mmol). The mixture was then left for 30 min. with stirring at 0° C., whereafter a solution of $Na_2CO_3$ (60 mmol) in $H_2O$ (50 ml) was added. The mixture was heated to room temperature, whereafter the organic phase was separated, dried and evaporated in vacuo. The residue was treated with ether, decanted, and the solution was evaporated to give the title compound as an oil.

The oil was processed without any further purification.

IR: $cm^{-1}$: 2160.

3-ethyl-5-isocyanomethyl-1,2,4-oxadiazole was prepared from 3-ethyl-5-formylaminomethyl-1,2,4-oxadizaole in a similar manner. IR: $cm^{-1}$: 2170.

EXAMPLE 5 a. Formylaminomethyl-carboxamideoxime

To 53.6 g (0.638 mol) N-formylamino-acetonitrile was added 0.55 mol fresly liberated hydroxylamine dissolved in 370 ml methanol. An ice bath was used to keep the temperature below 20° C. during addition. The solution was allowed to stand at room temperature overnight, whereafter it was evaporated to give the title compound as pale crystals.

Decomp. 104°–110° C.

b. 3-Formylaminomethyl-5-ethyl-1,2,4-oxadiazole

A mixture of 70 ml ethyl propionate, 20 g formylaminomethylcarboxamideoxime, 1 g sodium and 30 g crushed mol. sieves (4 Å) was refluxed in 300 ml abs. EtOH for 5 hours. The reaction mixture was filtered and the filtrate was evaporated. The oily residue was suspended in 300 ml $CHCl_3$, filtered, and the filtrate was evaporated to give the title compound as an oil.

HNMR (60 HMZ, $CDCl_3$) o' (ppm): 1.4(3H, t, J=8 Hz), 2.9(2H, q, J=Hz), 4.55 (2H, s), 7.8 (1H, broad-NH), 8.25 (1H, s).

The following compounds were synthesized from the appropriate ethyl esters:

3-Formylaminomethyl-5-cyclopropyl-1,2,4-oxadiazole
H-NMR (60 MHz, $CDCl_3$) o' (ppm): 1.2 (4H, m), 2.8 (1H, m), 4.5 (2H, d, J=6 Hz), 7.8 (1H, broad-NH), 8.2 (1H, s).

3-Formylaminomethyl-5-methyl-1,2,4-oxadiazole
H-NMR (60 MHz, $CDCl_3$) o' (ppm): 2.6 (3H, s), 4.6 (2H, d, J=3 Hz), 7.4 (1H, broad-NH), 8.25 (1H, s).

3-Formylaminomethyl-5-methoxymethyl-1,2,4-oxadiazole H-NMR (60 MHz, $CDCL_3$) o' (ppm): 3.5 (3H, s), 4.7 (4H, s+d, J=6 Hz), 7.8 (1H, broad-NH), 8.25 (1H, s).

c. 5-Cyclopropyl-3-isocyanomethyl-1,2,4-oxadiazole

A stirred solution of 5-cyclopropyl-3-formylaminomethyl-1,2,4-oxadiazole (60 mmol) and triethylamine (176 mmol) in $CH_2Cl_2$ (100 ml) was charged dropwise with $POCl_3$ (60 mmol) at 0° C. The mixture was then left for 30 min. with stirring at 0° C., whereafter a solution of $Na_2CO_3$ (60 mmol) in $H_2O$ (50 ml) was added. The mixture was heated to room temperature, whereafter the organic phase was separated, dried and evaporated in vacuo. The residue was treated with ether, decanted and the solution was evaporated to give the title compound as an oil.

The oil was processed without any further purification.

IR: $cm^{-1}$: 2160.

5-Ethyl-3-isocyanomethyl-1,2,4-oxadiazole, 5-methyl-3-isocyanomethyl-1,2,4-oxadiazole, and 5-methoxymethyl-3-isocyanomethyl-1,2,4-oxadiazole are prepared in a similar manner. All compounds are oils and are characterized by their IR stretching band at 2160 cm$^{-1}$.

Pharmaceutical Compositions and Method of Treating

The compounds of this invention can be used for the formulation of pharmaceutical preparations, e.g., for oral and parenteral administration to mammals including humans, in accordance with conventional methods of galenic pharmacy.

Conventional excipients are such pharmaceutically-acceptable organic or inorganic carrier substances suitable for parenteral or enteral application which do not deleteriously affect or react with the active compounds.

Examples of such carriers are water, salt solutions, alcohols, polyethylene glycols, polyhydroxyethoxylated castor oil, gelatine, lactulose, amylose, magnesium stearate, talc, silicic acid, fatty acid monoglycerides and diglycerides, pentaerythritol fatty acid esters, hydroxymethycellulose, and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances, and the like, which do not deleteriously effect or react with the active compounds.

For parenteral application, particularly suitable are injectable solutions or suspensions, preferably aqueous solutions with the active compound dissolved in polyhydroxylated castor oil.

Ampoules are conveniently unit dosages.

For oral application, particularly suitable are tablets, dragees, or capsules having a talc and/or a carbohydrate carrier or binder or the like, the carrier preferably being lactose and/or corn starch and/or potato starch. A syrup, elixir, or the like can be used when a sweetened vehicle can be employed.

Generally, the compounds of this invention are dispensed in unit dosage form comprising 0.05–100 mg in a pharmaceutically-acceptable carrier per unit dosage.

The dosage of the compounds according to this invention is 0.1–300 mg/day, preferably 1–30 mg/day, when administered to patients, e.g. humans, as a drug.

A representative tablet which may be prepared by conventional tabletting techniques contains:

Active compound 1.0 mg
Lactosum 67.8 mg Ph. Eur.
Avicel (microcrystalline cellulose) 31.4 mg
Amberlite IRP 88 1.0 mg
Magnesii stearas 0.25 mg Ph. Eur.

In conclusion, from the foregoing, it is apparent that the present invention provides novel oxadiazolyl imidazobenzodiazepine compounds which are useful for the amelioration of central nervous system disorders related to benzodiazepine receptors, especially as anticonvulsants, anxiolytics, and nootropics, having the aforesaid highly advantageous properties.

Further, a new synthesis is provided by the present invention, as well as a new intermediate therefor.

It is to be understood that the invention is not to be limited to the exact details of operation, or to the exact compounds, compositions, methods, procedures, or embodiments shown and described, as obvious modifications and equivalents will be apparent to one skilled in the art, and the invention is therefore to be limited only by the full scope of the appended claims.

We claim:

1. A method of preparing a compound according to formula (I),

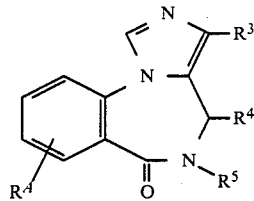

wherein R$^3$ has the formula

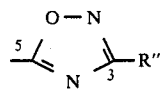

wherein
R″ is C$_{1-6}$ alkyl, C$_{1-6}$, or C$_{3-6}$ cycloalkyl;
R$^4$ is hydrogen;
R$^5$ is C$_{1-6}$ alkyl or R$^4$ and R$^5$ together form a 2–4 membered alkylene bridge; and R$^A$ is C$_{1-6}$ alkyl, C$_{1-6}$ alkoxy, or C$_{1-3}$ trifluoroalkyl, characterized in reacting a compound having the general formula XI

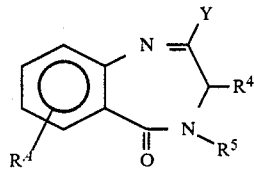

wherein R$^4$, R$^5$ and R$^A$ have the meanings defined above, and Y is a leaving group, with a compound having the formula XII $$CN-CH_2-R^3 \qquad (XII)$$

wherein R$^3$ has the meaning

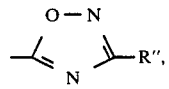

R″ being C$_{1-6}$alkyl or C$_{3-6}$cycloalkyl, to form a compound having the formula I.

* * * * *

UNITED STATES PATENT AND TRADEMARK OFFICE
CERTIFICATE OF CORRECTION

PATENT NO. : 4,772,696        Page 1 of 2

DATED : September 20, 1988

INVENTOR(S) : Frank Wätjen and Mogens Engelstoft

It is certified that error appears in the above-identified patent and that said Letters Patent is hereby corrected as shown below:

Title Page [75] Inventors:; delete "John B. Hansen, Lyngby; Leif H. Jensen, Hellerup,"

Title Page [56] References Cited; change

"FOREIGN PATENT DOCUMENTS 150040 7/1985 European Pat. Off. .... 540/498"  to read the following:

—           U.S. PATENT DOCUMENTS

| | | | |
|---|---|---|---|
| 4,031,079 | 6/1977 | Mohrbacher et al. | 540/509 |
| 4,316,839 | 2/1982 | Gerecke et al. | 540/498 |
| 4,359,420 | 11/1982 | Gerecke et al. | 540/498 |
| 4,435,403 | 3/1984 | Braestrup | 546/86 |
| 4,507,313 | 3/1985 | Braestrup et al. | 514/220 |

FOREIGN PATENT DOCUMENTS

| | | | |
|---|---|---|---|
| 0245 | 1/1985 | Denmark | 540/498 |
| 0027214 | 4/1981 | European Pat. Off. | 540/498 |
| 0054507 | 6/1982 | European Pat. Off. | 546/86 |
| 0109921 | 5/1984 | European Pat. Off. | 540/498 |
| 150040 | 7/1985 | European Pat. Off. | 540/498 |

OTHER PUBLICATIONS

Squires, R. F., et al., Nature (London), 266, pp. 732-734 (1977).
Hartman, G.D., et al., Synthesis, 10, pp. 681-682 (1976). --

(See Request for filing a Divisional Application Under 37 CFR 1.60 - item #13 (Prior Art Statement with all references cited, in the parent case) - Also see, Office Action dated 5/27/88, acknowledges references received). - Paper #12

UNITED STATES PATENT AND TRADEMARK OFFICE
CERTIFICATE OF CORRECTION

PATENT NO. : 4,772,696

DATED : September 20, 1988

INVENTOR(S) : Frank Wätjen and Mogens Engelstoft

It is certified that error appears in the above-identified patent and that said Letters Patent is hereby corrected as shown below:

Title Page [57] ABSTRACT, second line below the second formula; insert a comma -- , -- after "alkyl" and insert a comma -- , -- after "alkoxymethyl"

Title Page [57] ABSTRACT, fifth line below the second formula; insert a comma -- , -- after "alkyl"

Col. 8, line 50; "midazo" should read -- imidazo --

Col. 8, line 53; "9H-imido" should read -- 9H-imidazo --

Col. 8, line 56; "-benzodiazepin-" should read -- -benzodiazepine- --

Col. 11, line 47; "-oxadizaol-" should read -- -oxadiazol- --

Col. 12, line 13; "oxadizaole" should read -- oxadiazole --

Col. 12, line 19; "fresly" should read -- freshly --

Col. 14, line 29; delete ", $C_{1-6}$," (second occurrence)

Signed and Sealed this

Twenty-fifth Day of April, 1989

Attest:

DONALD J. QUIGG

Attesting Officer

Commissioner of Patents and Trademarks